United States Patent [19]
White

[11] Patent Number: 5,580,244
[45] Date of Patent: Dec. 3, 1996

[54] METHOD AND APPARATUS FOR TAKING DENTAL IMPRESSIONS

[76] Inventor: Dennis J. White, 51 Nostrand Rd., Cranbury, N.J. 08512

[21] Appl. No.: 396,478

[22] Filed: Mar. 2, 1995

[51] Int. Cl.$^6$ ................................................. A61C 9/00
[52] U.S. Cl. ............................ 433/37; 433/44; 433/47
[58] Field of Search ............................ 433/37, 46, 47, 433/74, 214, 44

[56] References Cited

U.S. PATENT DOCUMENTS

| | | | |
|---|---|---|---|
| 77,773 | 5/1868 | Smith et al. | 433/47 |
| D. 281,532 | 11/1985 | Weissman | D24/10 |
| 1,179,317 | 4/1916 | Hurrey | 433/47 |
| 1,323,832 | 12/1919 | Chige | 433/46 |
| 1,437,844 | 12/1922 | Henderson | 433/47 |
| 1,445,499 | 2/1923 | Douglass | 433/47 |
| 1,611,152 | 12/1926 | Backus | 433/47 |
| 2,043,294 | 6/1936 | Kalvin | 433/47 |
| 2,089,265 | 8/1937 | Kalvin | 433/46 X |
| 2,758,374 | 8/1956 | Fisher | 32/17 |
| 4,382,785 | 5/1983 | Lococo | 433/36 |
| 5,320,529 | 6/1994 | Pompa | 433/76 |

OTHER PUBLICATIONS

Alvin V. Pensler, D.D.S "Combined Bite Update for Good Impressions" Dentistry Today, Feb. '88.
R. W. Wassell, M. Sc. et al. "The accuracy of polyVinyl siloxane impressions" J. Prosthetic Dent 1991; 65:748–757.
A. J. Hunter, B.D.S. "Gingival Margins for Crowns" J. Prosthetic Dent. 1990, 64:636–641.
Glenn Gordon, D.D.S., et al. "The effect of tray selection on the accuracy of elastomeric impress mat" J. Pros. Dent. 1990; 63 12–15.

Primary Examiner—Nicholas D. Lucchesi

[57] ABSTRACT

An improved dental impression tray fabricated with vertical rests that anchor onto predetermined areas of the mouth to allow stabilization of tray while impression material sets. This disclosure also provides for a venting of selected teeth to the outside air to eliminate damaging force of vacuum on freshly cured material when tray is lifted. More specifically, the practitioner fills the impression tray with moldable material and seats fully into the mouth. Venting pins are immediately fitted through impression tray and impression material and seated onto the occlusal surfaces of the teeth. After the impression material has set, venting pins are removed. The impression tray is then lifted vertically and removed.

6 Claims, 5 Drawing Sheets

5,580,244

METHOD AND APPARATUS FOR TAKING DENTAL IMPRESSIONS

BACKGROUND OF THE INVENTION

1. Field of the Invention

This invention relates to taking accurate dental impressions, from which indirect dental castings are fabricated.

2. Description of the Prior Art

Heretofore, impression trays have solid or perforated walls designed to cup over teeth. Dental impression trays are used to carry impression material to areas of the mouth and are used to support the moldable material until it cures. The tray is then utilized to remove the set material from the mouth.

A hardening material, such as dental stone or epoxy, is subsequently poured into the impression. Thus, a model is obtained when the die material has hardened and then recovered from the impression material. From this model, a prosthesis is fabricated to fit this area of the mouth.

Removing impression trays can be difficult because of suction existing between impression material and tissue surfaces while lifting away from oral structures. A very strong suction may distort the impression. Elasticity limits of impression material are often exceeded leaving an unknowingly distorted impression.

Present trays do not provide for venting of the impression when the tray is lifted. Resultant vacuum trap over teeth causes undue pressure on soft, fresh cured material.

Also, the tray may shift during setting by an inadvertent hand movement of the dentist or by the patient swallowing and moving the tongue. A tray, jarred during setting, will yield unreliable results. Dentists today must support the tray by hand while impression material sets in the patient's mouth. Present trays do not provide for stabilization against tooth structures.

In U.S. Pat. No. 5,320,529, Pompa discloses a device for an implant drill guide. Guides utilized are in a splint, not in an impression tray. The operation is different from the present invention. Pompa's invention relates to drilling in a controlled area.

In U.S. Pat. No. 4,382,785, Lococo discloses a tray to receive impression material through orifices along the top, but does not provide for venting.

3. Objects of the Invention

An object of this invention is to produce a dental impression tray which will fit securely in one location. The tray rests on selected teeth and resists movement while impression material is setting.

Another object of the present invention is to allow certain selected areas of the impression tray to be vented. An open airway from occlusal surfaces of teeth to ambient air is established before the tray is removed.

Another object of the present invention is to provide an impression tray which increases accuracy and which provides a predictable fit, leaving the dentist with a more controllable means of fabricating a quality casting.

Another object of the present invention is to provide an impression tray which will aid dentists and laboratory technicians in the process of fabricating restorations.

DETAILED DESCRIPTION OF THE PREFERRED EMBODIMENT

Figure 1:
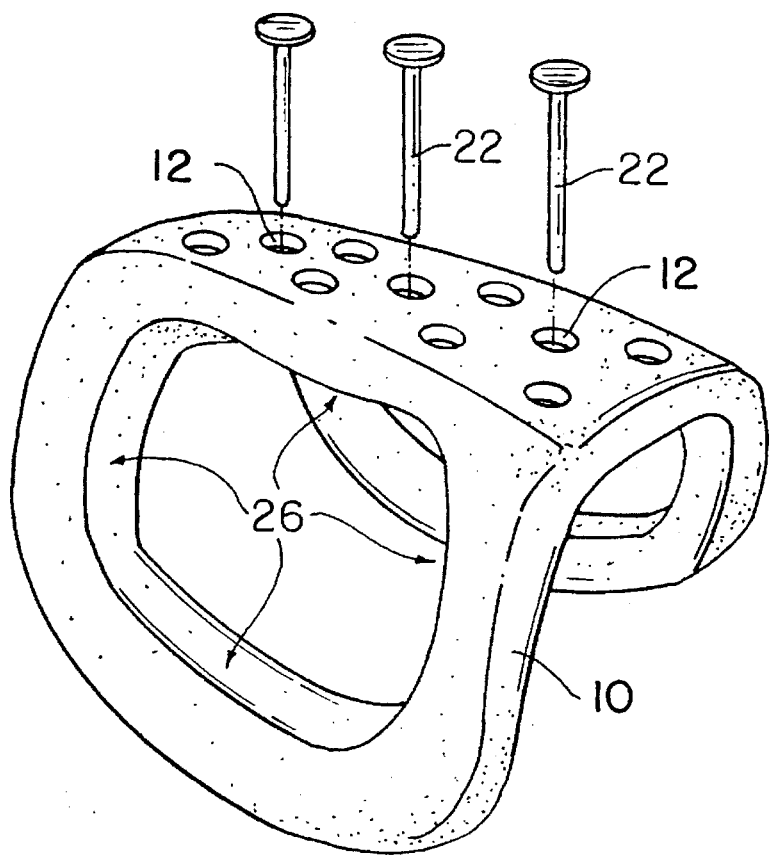
FIG. 1 is a perspective view of the impression tray of the present invention.
Figure 2:
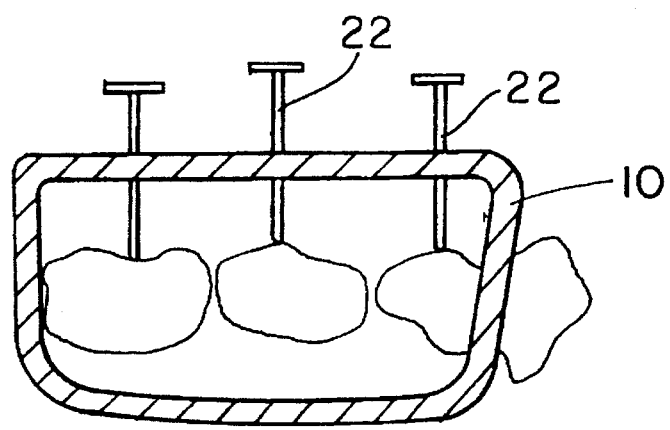
FIG. 2 is a lateral view of the impression tray in place over teeth, with removable venting pins in contact with occlusal surfaces of the teeth.
Figure 3:
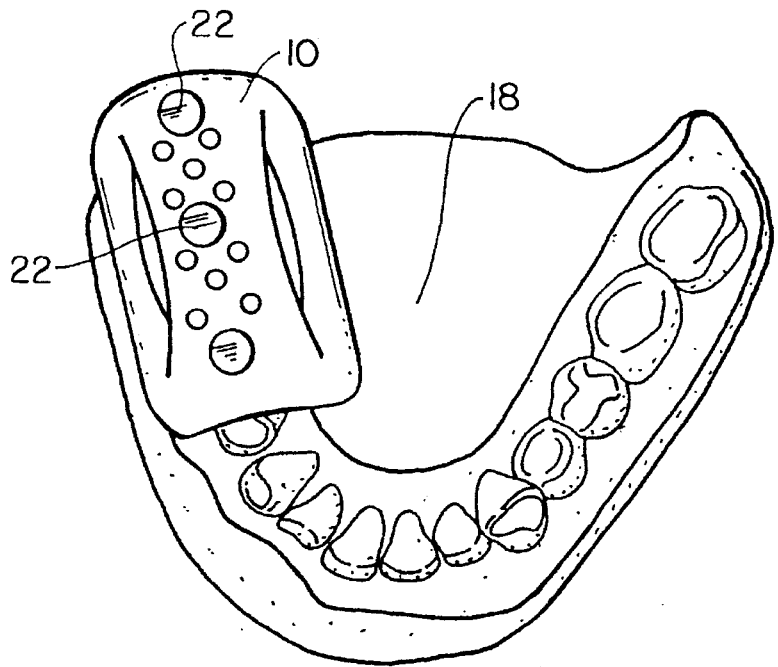
FIG. 3 is a top view of the impression tray in place over mandibular teeth with the venting pins in place.

Referring to the drawings in general, and to FIGS. 1–9 in particular, a dental impression tray according to the present invention is shown.

FIG. 1 shows a diagonal view of the impression tray 10 with separate removable venting pins 22 which are held in vent holes 12 formed in the top surface of the tray. On a dental study model 18, an appropriate size tray is fitted over teeth to be restored, and is selected for the case.

Figure 4:
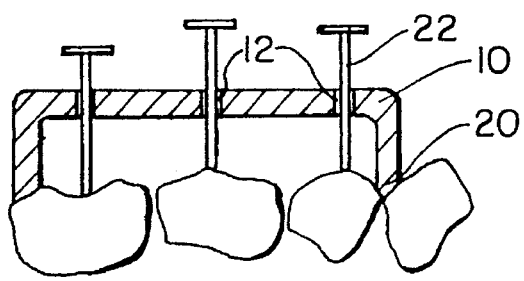
FIG. 4 is a side cross section view of the impression tray in place over the teeth.
Figure 5:
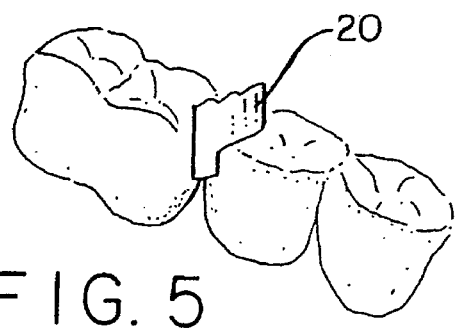
FIG. 5 is a perspective view of an occlusal rest portion of the tray which conforms to the surface of a tooth.
Figure 6:
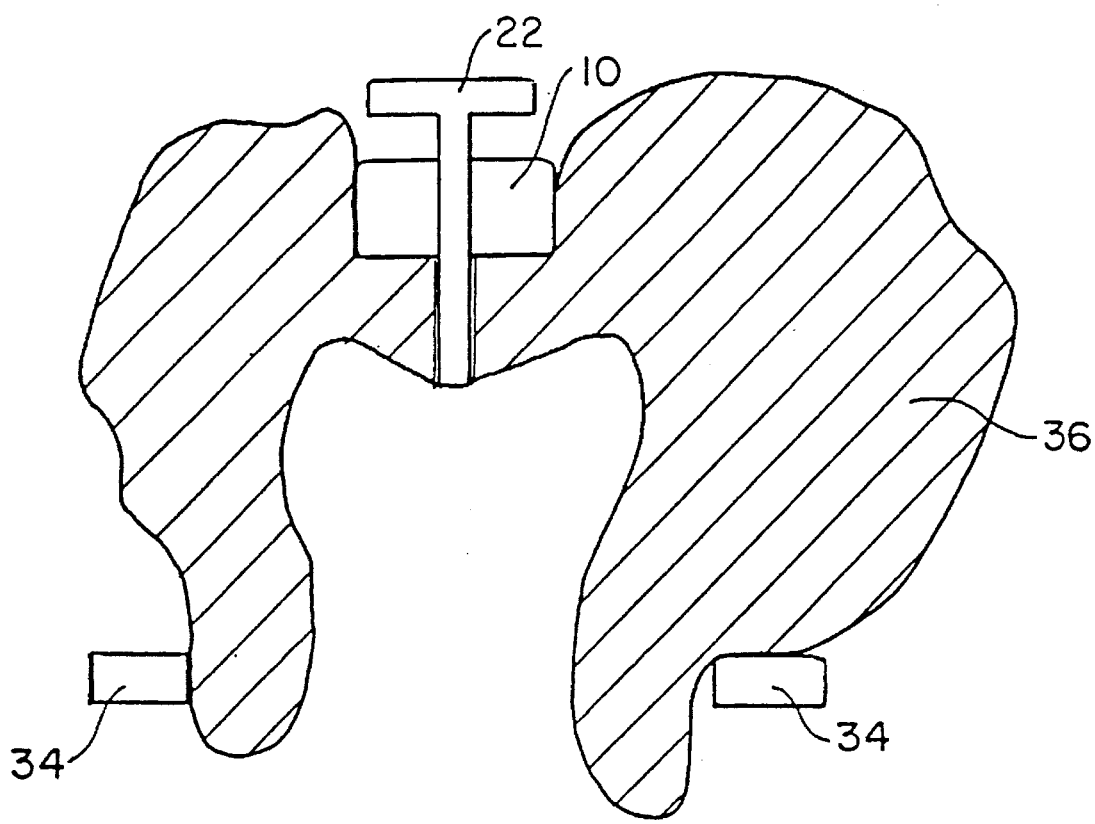
FIG. 6 is a frontal cross section view of the impression tray of the present invention with the tray in place over teeth, with impression material.
Figure 7:
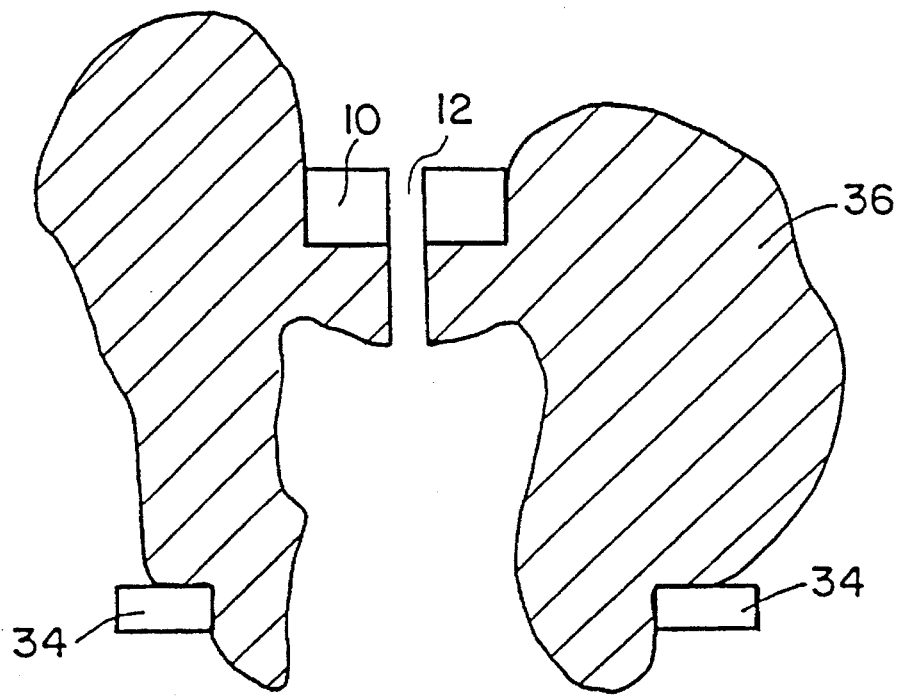
FIG. 7 is a frontal view of a cross section of the impression tray of the present invention with the tray in place over the teeth, with impression material, with the venting pins removed.

Occlusal rests 20, are then formed with self curing methylmethacrylate or other moldable material to give a definitive seating position for the tray, as shown in FIG. 4. These rests are also designed to support the tray at a suitable occlusal height, and are also designed to provide adequate stability so that the tray is well anchored during curing time of the impression material. FIG. 5 shows how the methylmethacrylate may be allowed to extend laterally over the contact area to assure tray stability. Removable pins 22 are placed in appropriate holes 12 in tray 10 over teeth to be vented as shown in FIG. 4.

Typically, vent pins 22 may be ⅛ inch in diameter. Vent holes 12 may also be ⅛ inch diameter and may accept an appropriate length of plastic tubing (not shown). This particular size tubing provides an inner diameter opening suitable to receive the shank of an ordinary friction grip bur. This ⅛ inch tubing is readily available in the dental industry and used in dental delivery units. The plastic tubing provides for a sturdy anchor for vent pins 22 when the impression tray is filled with impression material, and also secures the pins when the tray is placed in the oral cavity, while providing for an accurate fit to allow for a smooth, controlled removal of pins 22 once the impression material has set.

Two vent pins 22 may be placed for each tooth, corresponding with buccal and lingual cusps. Also, venting pins 22 could be custom molded to accept a ligature of dental floss. Optionally, holes 12 not occupied by vent pins 22 may be closed off with suitable material, or left to be filled with impression material.

The impression tray 10 may also be provided with buccal and/or lingual windows 26, as shown in FIG. 1. These windows provide for a lifting shelf 34 (FIGS. 6 and 7) which aids in the removal of the impression tray, allowing the impression material 36 to be lifted instead of pulled, thereby putting less stress on the adhesive junction between the impression material and the tray.

Figure 8:
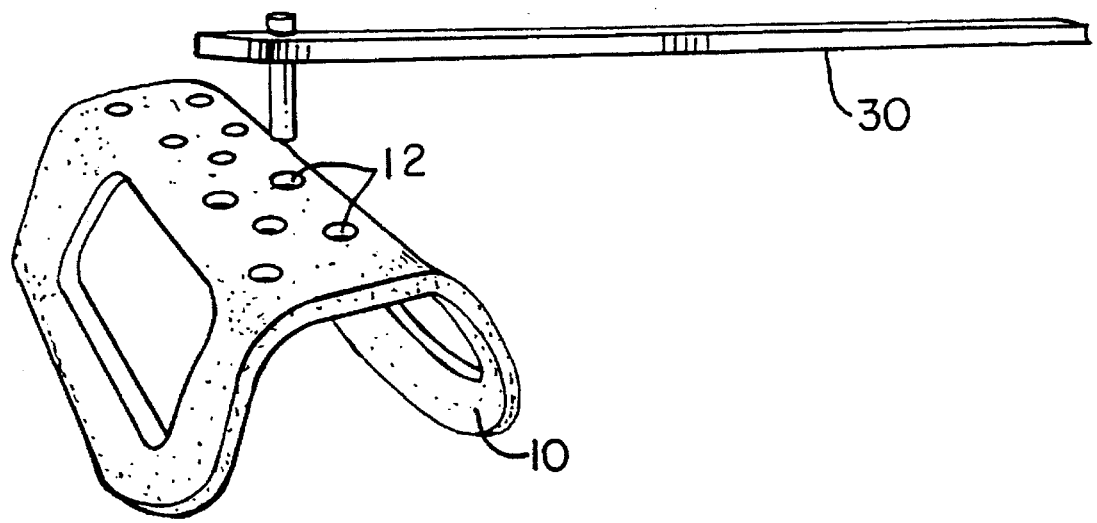
FIG. 8 is a perspective view of the impression tray of the present invention with a removable stabilizer arm.
Figure 9:
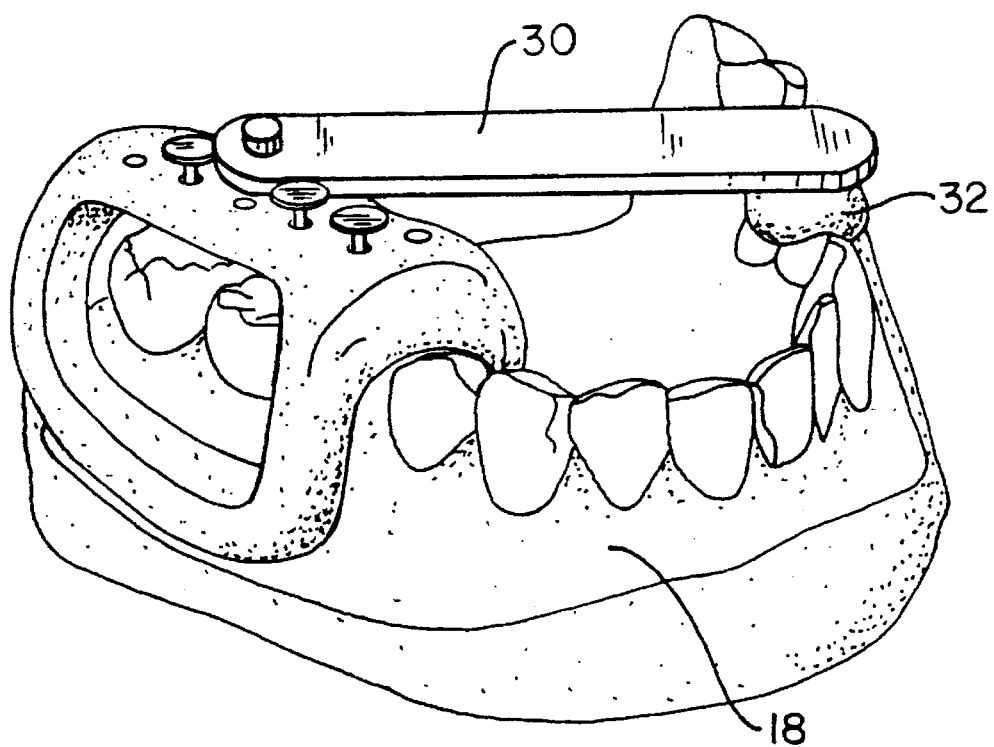
FIG. 9 is a top perspective view of the impression tray in place with the stabilizer arm.
Figure 10:
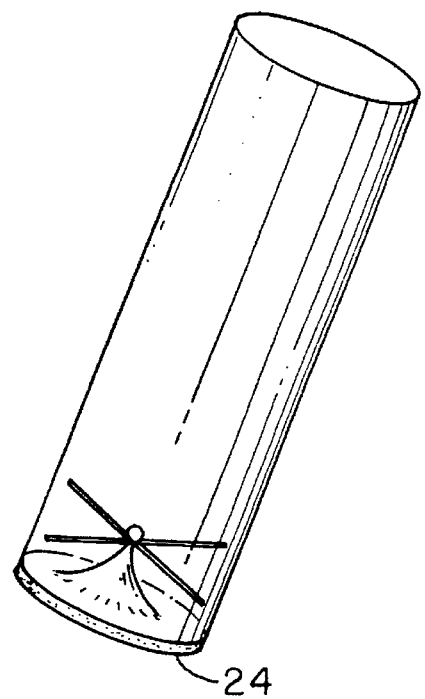
Figure 11:
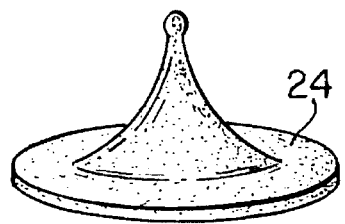
Figure 12:
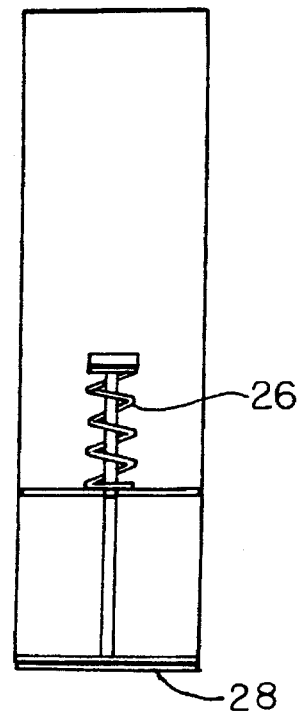

FIGS. 8 and 9 show the tray 10 of the present invention fitted with a cross arch stabilizer bar 30. The stabilizer bar 30 may be attached utilizing any of the vent holes 12, on top of the tray 10. An occlusal rest 32 (FIG. 9) may be used to anchor the stabilizer bar 30 to a distant tooth. The length of the bar 30 may be modified as needed.

The impression tray of the present invention may be custom fabricated in a dental laboratory. Relief wax is first applied to model teeth, which will represent areas later occupied by impression material. Moldable tray material is placed over the wax and is extended far enough beyond to give sufficient strength and extension to the tray borders. After the tray is set, relief wax is removed and the tray is marked to receive vent holes over selected teeth. The holes are drilled in size to produce a sliding fit of the removable vent pins.

Conclusions, Ramifications and Scope

Thus, the reader can see the impression tray disclosed herein is versatile and can be used for onlays, crowns and bridges, and can be used in any area of the mouth. While only a single embodiment of the present invention has been shown and described, it is to be understood that many changes and modifications may be made thereunto without departing from the spirit and scope of the invention as defined in the appended

I claims:

1. A dental impression tray for taking dental impressions, comprising: a U-shaped body portion formed of a material suitable for use within the oral cavity, the body portion having an upper surface and a pair of side surfaces each extending at an angle from the upper surface, said body portion having a plurality of vent holes formed in said upper surface, with at least one vent pin removably held in at least one of said vent holes, said tray further comprising occlusal stability rests formed on anocclusal surface thereof, to allow proper seating of said tray within an oral cavity.

2. The dental impression tray of claim 1, further comprising a plurality of said vent pins located in selected ones of said plurality of vent holes.

3. The dental impression tray of claim 2, further comprising a window located in each of said side surfaces.

4. The dental impression tray of claim 1, further comprising a window located in each of said side surfaces.

5. The dental impression tray of claim 4, further comprising a stabilizer bar adapted to be held in one of said vent holes, for stabilizing said tray in the oral cavity.

6. The dental impression tray of claim 1, further comprising a stabilizer bar adapted to be held in one of said vent holes, for stabilizing said tray in the oral cavity.

* * * * *